United States Patent [19]

Yoshimura et al.

[11] Patent Number: 4,921,948
[45] Date of Patent: May 1, 1990

[54] SIALOSYL GLYCERIDE AND PROCESS FOR PRODUCING THE SAME

[75] Inventors: Shoji Yoshimura, Iruma; Yuzi Matsuzaki, Kawagoe; Mamoru Sugimoto, Tokyo; Masayoshi Ito, Kunitachi; Tomoya Ogawa, Musashino, all of Japan

[73] Assignee: Mect Corporation, Tokyo, Japan

[21] Appl. No.: 319,064

[22] Filed: Mar. 6, 1989

[30] Foreign Application Priority Data

Mar. 10, 1988 [JP] Japan .................................. 63-56884

[51] Int. Cl.$^5$ ....................... C07H 15/00; C07G 3/00; C07G 17/00
[52] U.S. Cl. ..................................... 536/18.2; 536/4.1; 536/17.2; 536/18.4; 536/18.5; 536/124
[58] Field of Search ....................... 536/18.2, 4.1, 17.2, 536/18.4, 18.5, 124

[56] References Cited

U.S. PATENT DOCUMENTS 4,618,675 10/1986 Lichtenthaler et al. ............. 536/4.1
4,694,076 9/1987 Ogawa et al. ...................... 536/17.2
4,797,477 1/1989 Yoshimura et al. ................ 536/18.2

FOREIGN PATENT DOCUMENTS 315973 11/1988 European Pat. Off. .
59-181298 10/1984 Japan .................................. 536/18.2

Primary Examiner—Ronald W. Griffin
Assistant Examiner—Everett White
Attorney, Agent, or Firm—Oblon, Spivak, McClelland, Maier & Neustadt

[57] ABSTRACT

The present application discloses a new sialosyl glyceride having the following formula, which compound is useful as a remedy for nervous diseases, has an excellent compatability with the living bodies, and is easily producible.

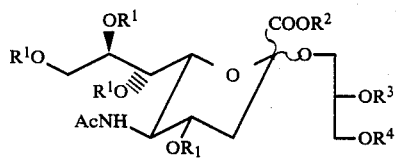

wherein $R^1$ represents a hydrogen atom or $XCH_2CO-$ (X being a halogen atom), $R^2$ represents an alkali metal, a hydrogen atom or a lower alkyl group, $R^3$ represents a hydrogen atom or $-CO(CH_2)mCH_3$, $R^4$ represents $-CO(CH_2)mCH_3$ amd m and n each represents a number of 0 to 30.

9 Claims, No Drawings

SIALOSYL GLYCERIDE AND PROCESS FOR PRODUCING THE SAME

BACKGROUND OF THE INVENTION

1. Field of the Invention:

The present invention relates to a sialosyl glyceride and a process for producing the same.

2. Description of the Prior Art

Many of diseases derived from lesions relating to the nervous system are intractable. The number of the remedies for these diseases are not so many. At present, ganglioside (trade name: Cronassial. Please see Japanese patent Unexamined Published application (hereinafter referred to as 'J. P. KOKAI') No. 52-34912), which is a natural glicolipid, and Mecobalamin (a kind of a vitamin) are clinically used.

However, the effects of them are yet insufficient and, therefore, the development of a more effective remedy has been eagerly demanded.

After intensive investigations made for the purpose of filling the demand, the applicant has developed sialosyl glycerolipids of the general formula:

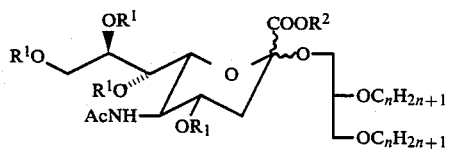

wherein $R^1$ represents a hydrogen atom or $CH_3CO-$, $R^2$ represents an alkali metal, a hydrogen atom or a lower alkyl group and n represents a number of 1 to 30 which are useful as remedies for the nervous diseases (Please see Japanese Patent Application No. 62-283491).

In general, natural compounds contain a higher ester bond content than ether bond content. However, the sialosyl glycerolipids have ether bonds in 1-position and 2-position of the glycerol. Therefore, these compounds not always have a sufficient compatibility with the living bodies and they are not always excellent with respect to the antigen-antibody reaction. In addition, since these compounds have the ether bonds, it is difficult to select a suitable protective group in the production of them. Thus, they cannot be easily produced for the above-described reasons.

SUMMARY OF THE INVENTION

An object of the present invention is to provide a new compound which is useful as a remedy for nervous diseases, which has an excellent compatibility with the living bodies, and which can be easily produced.

After intensive investigations made for the purpose of attaining the above-described object of the invention, the inventors have found that the object can be attained by introducing an ester bond into 1-position or 2-position of a glycerol moiety of a sialic acid-containing lipid derivative. The present invention has been completed on the basis of this finding.

Namely, the present invention relates to:

1. sialosyl glyceride of the general formula:

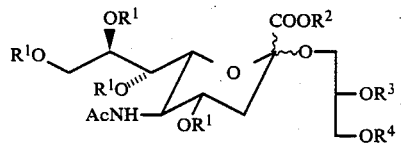

wherein $R^1$ represents a hydrogen atom or $XCH_2CO-$ (X being a halogen atom), $R^2$ represents an alkali metal, a hydrogen atom or a lower alkyl group, $R^3$ represents a hydrogen atom or $-CO(CH_2)_mCH_3$, $R^4$ represents $-CO(CH_2)_nCH_3$ and m and n each represents a number of 0 to 30, 2. a process for producing a sialosyl glyceride of the general formula:

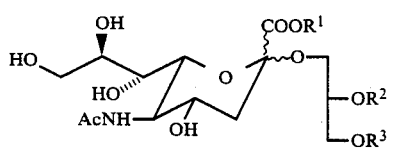

wherein $R^1$ represents a lower alkyl group, $R^2$ represents a hydrogen atom or $-CO(CH_2)_mCH_3$, $R^3$ represents $-CO(CH_2)_nCH_3$ and m and n each represents a number of 0 to 30, characterized by demonohalogenoacetylating a compound of the general formula:

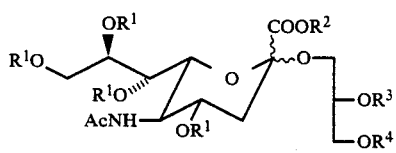

wherein $R^1$ represents $XCH_2CO-$ (X being a halogen atom), $R^2$ represents a hydrogen atom or an alkyl group, $R^3$ represents a hydrogen atom or $-CO(CH_2)_mCH_3$, $R^4$ represents $-CO(CH_2)_nCH_3$ and m and n each represents a number of 0 to 30, and 3. a process for producing a sialosyl glyceride of the general formula:

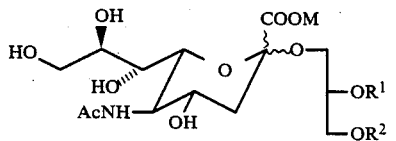

wherein M represents an alkali metal, $R^1$ represents a hydrogen atom or $-CO(CH_2)_mCH_3$, $R^2$ represents $-CO(CH_2)_nCH_3$ and m and n each represents a number of 0 to 30 characterized by treating a compound of the general formula:

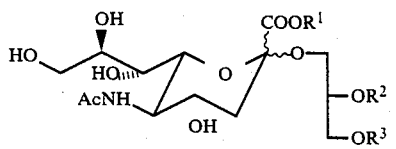

wherein $R^1$ represents a lower alkyl group, $R^2$ represents a hydrogen atom or $-CO(CH_2)_mCH_3$, $R^3$ represents $-CO(CH_2)_nCH_3$ and m and n each represents a number of 0 to 30,
with an alkaline aqueous solvent.

Now the detailed description will be made on the present invention.

The alkali metal $R^2$ in the formula [I] is preferably sodium and the lower alkyl group is preferably methyl group.

m and n in the formula [I] each is preferably 6 to 20, particularly 14 to 16.

The process for producing the compound of the present invention will be described with reference to the following scheme (I):

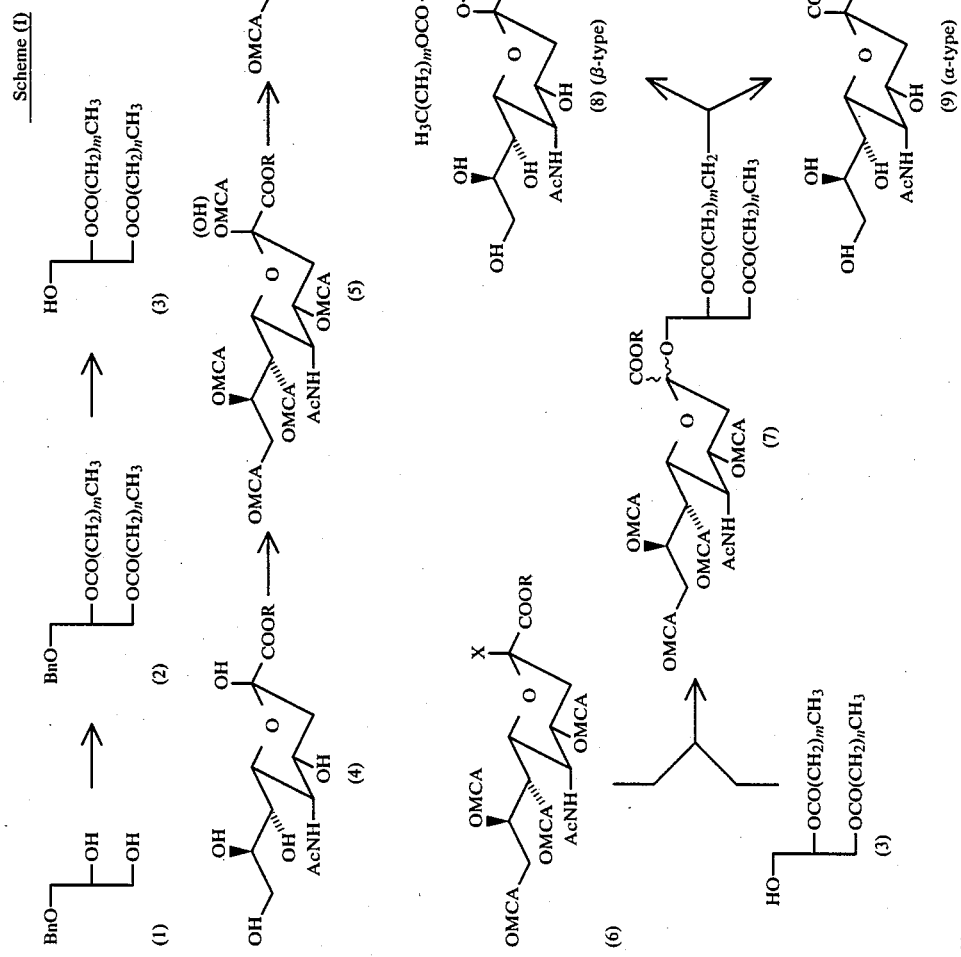

Compound (2) is produced by esterifying Compound (1) with an acid halide of the formula:

CH₃(CH₂)ₙCOX wherein n represents a number of 0 to 30 and X represents a halogen atom,
such as tetradecanoyl chloride in the presence of, if necessary, a tertiary base such as triethylamine in a solvent such as anhydrous pyridine, dichloromethane, dichloroethane, THF, ethyl acetate, DMF or chloroform at 0° to 80° C., for example, room temperature, for about 6 hrs. to 1 week. The alkyl moiety of the acid chloride may have a branch. The mixture of the acid halides can be also used. From the viewpoint of the yield, X is preferably a chlorine atom. Compound (1) is commercially available on the market and processes for producing it are well known. Although the benzyl group of Compound (1) can be replaced with various substituents, the benzyl group is much preferred from the viewpoint of the yield.

Compound (3) is formed by eliminating the benzyl group from Compound (2). In this step, the benzyl group is eliminated by treating Compound (2) in the presence of a catalyst such as Pd-C (palladium on active carbon) in a solvent such as ethyl acetate, methanol, ethanol, THF or acetic acid in hydrogen stream at 0° to 40° C., for example, around room temperature, for 5 hrs. to 5 days.

Compound (4) is produced from N-acetylneuraminic acid (sialic acid). Sialic acid used as the starting material and process for the production of Compound (4) from sialic acid are well known. Compound (4) per se is also well known and commercially available on the market.

Compound (5) can be produced by reacting Compound (4) with a monohalogenated anhydrous acetic acid such as monochloroacetic acid. The reaction is conducted usually under anhydrous conditions. As the solvent, DMF is preferred. The temperature is −10° C. to 40° C., usually around room temperature. The reaction time is usually about 1 hr. to 3 days.

Compound (6) can be produced by reacting Compound (5) with a gaseous hydrogen halide in a solvent under cooling with ice. The solvents usable herein include acetyl halides such as acetyl chloride, as well as dichloroethane and dichloromethane. The hydrogen halide is preferably gaseous hydrochloric acid. After saturation with the gaseous hydrogen halide, the reaction is continued usually at −20° C. to 30° C. for about 5 hrs. to 5 days.

Compound (7) can be produced by reacting Compound (3) with Compound (6) in the presence of a catalyst such as mercury (II) bromide or mercury (II) cyanide in a solvent such as dichloromethane, dichloroethane, DMF, acetonitrile, CH₃NO₂ or THF at −10° C. to 50° C. for, for example 30 mins. to 10 hrs. From the viewpoint of the yield, the X group of Compound (6) is preferably a chlorine atom and the R group of the carboxylate is preferably methyl group.

Compound (7) thus produced is in the form of a mixture of α-type and β-type thereof.

Compound (7) thus produced is then reacted with thiourea or the like to eliminate the monohalogenated acetyl group and thereby to obtain a mixture of Compound (8) and (9), i.e. the mixture of α-type compound and β-type compound. The solvent is pyridine, ethanol, methanol, THF or the like. The temperature is 30° to 100° C., preferably around room temperature. The reaction time is 10 mins. to 3 days, particularly preferably 30 mins. to 1 day.

Compounds (8) and (9) are treated with an alkali metal hydroxide such as NaOH in a solvent such as THF to form Compounds (10) and (11), respectively. The reaction is conducted usually under cooling with ice. The reaction time is about 10 mins. to 2 days, for example about 30 mins. to 1 day.

The following examples will further illustrate the present invention.

EXAMPLE 1

Production of Compound (2) (m, n=12)

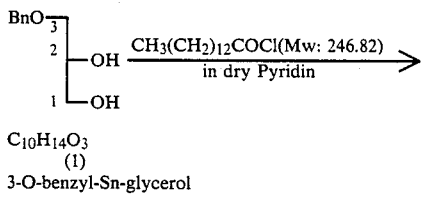

C₁₀H₁₄O₃
(1)
3-O-benzyl-Sn-glycerol

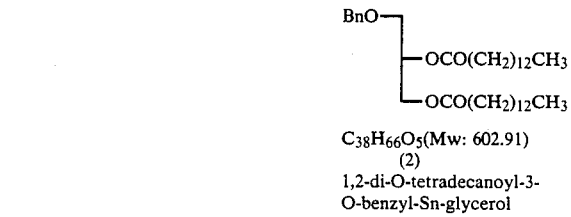

C₃₈H₆₆O₅(Mw: 602.91)
(2)
1,2-di-O-tetradecanoyl-3-O-benzyl-Sn-glycerol 4.30 g (17.4 mmol) of tetradecanoyl chloride was added to 20 ml of a solution of 1.27 g (6.98 mmol) of Compound (1) in anhydrous pyridine and the mixture was stirred at room temperature for three days. The solvent was distilled off and the reaction liquid was dissolved in 300 ml of ethyl acetate. The solution was washed with a 0.1 N HCl solution, a saturated sodium hydrogencarbonate solution and saline solution, and then dried over anhydrous magnesium sulfate. The solvent was evaporated to obtain 6.2 g of an oily product. This product was purified by silica gel column chromatography (with 400 g of Kieselgel 60 (a product of Merck Co.), hexane/ethyl ether ratio=20:1 to 10:1) to obtain 3.88 g (6.44 mmol) of Compound (2). Yield: 92.2%.

The physical properties of Compound (2) were as follows:

| 500 MHz, ¹H-NMR, CDCl₃, | TMS, δ |
|---|---|
| 0.879 (3 H, t, J = 7.0 Hz | C$\underline{H}_3$) |
| 0.883 (3 H, t, J = 7.0 Hz | C$\underline{H}_3$) |
| 1.254 (40 H, m, | C$\underline{H}_2$ × 20) |
| 1.600 (4 H, m, | C$\underline{H}_2$-3' × 2) |
| 2.275 (2 H, t, J = 7.7 Hz | C$\underline{H}_2$-2') |
| 2.317 (2 H, t, J = 7.5 Hz | C$\underline{H}_2$-2') |
| 3.578 (1 H, dd, J = 11.6, 5.1 Hz | H-3) |
| 3.602 (1 H, dd, J = 11.6, 5.1 Hz | H'-3) |
| 4.190 (1 H, dd, J = 11.9, 6.4 Hz | H-1) |
| 4.344 (1 H, dd, J = 11.9, 3.9 Hz | H'-1) |
| 4.538 (2 H, dd, J = 20.5, 12.1 Hz | φ-C$\underline{H}_2$—) |
| 5.239 (1 H, m, | C$\underline{H}$-2) |

EXAMPLE 2

Production of Compound (3) (m, n=12)

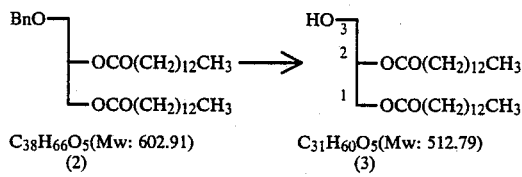

3.08 g (5.10 mmol) of Compound (2) was dissolved in 40 ml of ethyl acetate. 300 mg of 10% palladium on active carbon was added to the solution and the mixture was stirred at room temperature under hydrogen atmosphere for two days. The reaction mixture was filtered through Celite. The residue was washed with chloroform. The filtrate was combined with the washing solution. The solvent was evaporated. The resulting residue was recrystallized from petroleum ether to obtain 2.51 g (4.89 mmol) of Compound (3). Yield: 95.9%.

The physical properties of Compound (3) were as follows:

| 500 MHz, $^1$H-NMR, CDCl$_3$, TMS | |
|---|---|
| 0.880 (6 H, t, J = 7.0 Hz | C$\underline{H}_3$ × 2) |
| 1.271 (40 H, m, | C$\underline{H}_2$ × 20) |
| 1.613 (4 H, m, | C$\underline{H}_2$-3' × 2) |
| 2.044 (1 H, m, | HO) |
| 2.322 (2 H, t, J = 7.5 Hz | C$\underline{H}_2$-2') |
| 2.344 (2 H, t, J = 7.5 Hz | C$\underline{H}_2$-2') |
| 3.729 (2 H, d, J = 4.4 Hz | C$\underline{H}_2$-3) |
| 4.236 (1 H, dd, J = 11.9, 5.7 Hz | H-1) |
| 4.319 (1 H, dd, J = 11.9, 4.6 Hz | H'-1) |
| 5.082 (2 H, m, | H-2) |

EXAMPLE 3

Production of Compound (5) (R=Me)

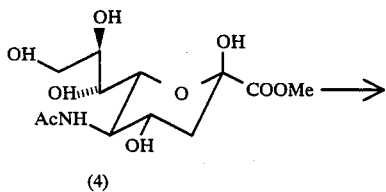

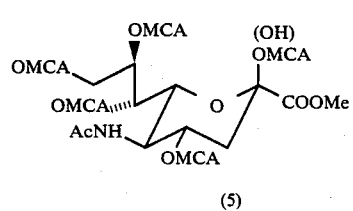

Methyl (5-acetamide-2,4,7,8,9-penta-O-chloroacetyl-3,5-dideoxy-β-D-glycero-D-galacto-2-nonulopyranosyl)onate 5.13 g (15.87 mmol) of Compound (4) was dissolved in 50 ml of anhydrous DMF. 1.53 g (19.04 mmol) of sodium hydrogencarbonate and 20.35 g (119.00 mmol) of anhydrous monochloroacetic acid were added to the solution and the mixture was stirred under argon atmosphere at room temperature for 6 hrs. The reaction mixture was poured into ice/water. An insoluble product was collected by filtration and dissolved in 500 ml of chloroform. The solution was washed with saline solution and dried over anhydrous magnesium sulfate. The solvent was evaporated. The resulting residue was purified with SiO$_2$ column chromatography (Wako Gel C-300, CHCl$_3$: MeOH =50:1) to obtain 4.8 g of penta- and tetramonochloroacetyl compound (5). Yield: 43.9%.

Compound (5) was used in the next step without purification.

EXAMPLE 4

Production of Compound (6) (R=Me, X=Cl)

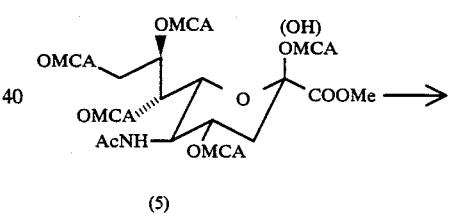

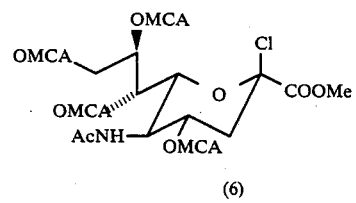

Methyl (5-acetamide-4,7,8,9-tetra-O-chloroacetyl-2-chloro-2,3,5-trideoxy-β-D-glycero-D-galacto-2-nonulopyranosyl)onate 1.80 g of Compound (5) was dissolved in 30 ml of acetyl chloride. The solution was saturated with gaseous hydrogen chloride under cooling with ice and stirred for two days in a closed vessel at room temperature. The solvent was distilled off and the residue was subjected to azeotropic distillation with toluene three times to obtain 1.6 g of Compound (6). Yield: 94.7%.

EXAMPLE 5

Production of Compound (7) (R=Me, m, n=12)

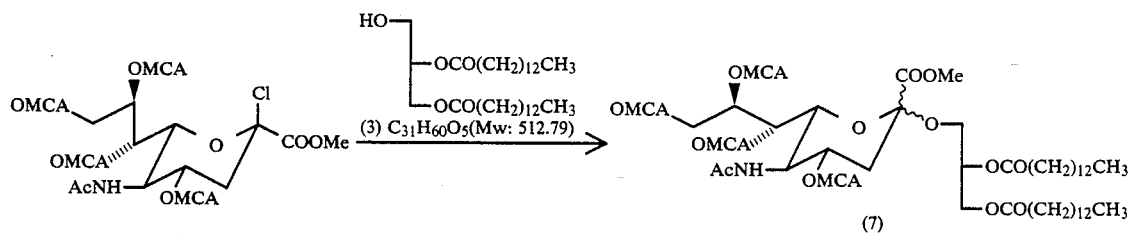

(6)
3-O-[Methyl(5-acetamide-4,7,8,9-tetra-O-chloroacetyl-3,5-dideoxy-α or β-D-glycero-D-galacto-2-nonulo-pyranosyl)onate]-1,2-di-O-tetradecanoyl-Sn-glycerol A mixture of 2.5 g of molecular sieves 4A, 1.24 g (4.89 mmol) of mercury (II) cyanide and 1.76 g (4.89 mmol) of mercury (II) bromide in chloroform was stirred for 15 mins. at room temperature. Then, 2.03 g (3.95 mmol) of Compound (3) was added to the suspension and the mixture was stirred under argon atmosphere at room temperature for 2 hrs.

The reaction mixture was cooled with ice. 15 ml of a solution of 1.60 g (2.47 mmol) of Compound (6) in anhydrous CHCl$_3$ was added to the reaction mixture, which was stirred at room temperature for 45 hrs. and then at 50° C. for additional 2 hrs. The reaction mixture was filtered through Celite. The filtrate was combined with the washing solution, and the solvent was evaporated in vacuum. 5.1 g of the thus obtained residue was chromatographed through silica gel (230 g of Wako Gel C-300, CHCl$_3$: EtOH=100:1) to give 1.92 g of a mixture of α- and β-type Compounds (7) including impurities. Since Compound (7) was unstable in the determination of the physical properties thereof (NMR), MCA groups were removed and the physical properties of Compounds (8) and (9) were determined.

In TCL of Compounds (7), the following spots were observed:

Re; β-type compound 0.78 (CHCl$_3$: MeOH=40:1, Merck HPTLC). α-type compound 0.58 (CHCl$_3$: MeOH=40:1, Merck HPTLC).

EXAMPLE 6

Production of Compounds (8) and (9) (R=Me, m, n=12)

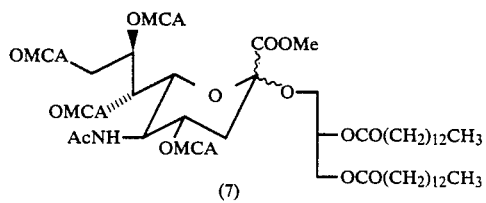

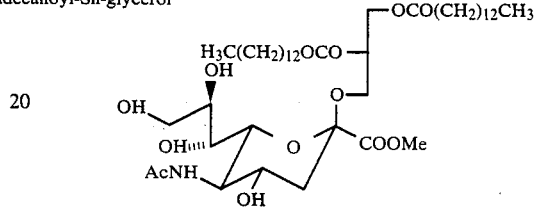

(8) C$_{43}$H$_{79}$O$_{13}$N(Mw: 818.07)
3-O-[Methyl(5-acetamide-3,5-dideoxy-β-D-glycero-D-gelacto-2-nonulopyranosyl)onate]-1,2-di-O-tetradecanoyl-Sn-glycerol (8)

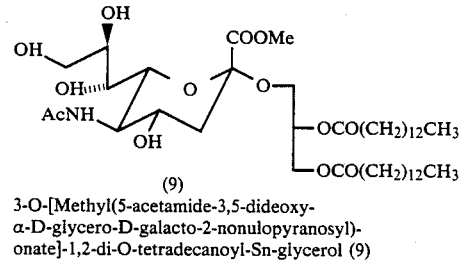

(9)
3-O-[Methyl(5-acetamide-3,5-dideoxy-α-D-glycero-D-galacto-2-nonulopyranosyl)-onate]-1,2-di-O-tetradecanoyl-Sn-glycerol (9)

1.74 g (1.55 mmol, of Compound (7) was dissolved in 20 ml of EtOH. 0.94 g (12.35 mmol) of thiourea and 4 ml of pyridine were added to the solution, which was stirred at room temperature for 4 hrs. and then under heating at 55° C. for 1 hr. The solvent was evaporated and CHCl$_3$ was added to the residue and filtrated to remove insoluble substance. The solvent was evaporated from the filtrate and the residue was chromatographed through silica gel (Wake Gel C-300, CHCl$_3$: MeOH=10:1) to give 45.3 mg of β-type compound (8), 111.5 mg of α-type compound (9), and 402.0 mg of a mixture of β-type compound (8) and α-type compound (9).

Yield: the mixture of β-type Compound (8) and 44.0%. α-type Compound (9):

The physical properties of Compound (8) were as follows:

| Rf: 0.47 (CHCl$_3$: MeOH = 10:1, Merck HPTLC) 500 MHz, $^1$H-NMR, CDCl$_3$, TMS, δ | |
|---|---|
| 0.880 (6 H, t, J = 7.0 Hz | C$\underline{H}_3$ × 2) |
| 1.256 (40 H, m, | C$\underline{H}_3$ × 20) |
| 1.600 (4 H, m, | C$\underline{H}_2$-3' × 2) |
| 1.792 (1 H, t, J = 12.1 Hz | H-3a ax) |
| 2.090 (3 H, S, | CH$_3$CONH) |
| 2.350 (4 H, m, | C$\underline{H}_2$-2' × 2) |
| 2.479 (1 H, dd, J = 13.2, 4.8 Hz | H-3a eq) |
| 3.783 (3 H, S, | COOC$\underline{H}_3$) |
| 4.238 (1 H, dd, J = 12.1, 5.5 Hz | H-1) |
| 4.319 (1 H, dd, J = 12.1, 4.6 Hz | H'-1) |

-continued

| Rf: 0.47 (CHCl₃: MeOH = 10:1, Merck HPTLC) 500 MHz, ¹H-NMR, CDCl₃, TMS, δ | |
|---|---|
| 6.260 (1 H, broad, | CH₃CON$\underline{H}$) |

The physical properties of Compound (9) were as follows:

| Rf: 0.44 (CHCl₃: MeOH = 10:1, Merck HPTLC) 500 MHz, ¹H-NMR, CDCl₃, TMS | |
|---|---|
| 0.880 (6 H, t, J = 7.0 Hz | C$\underline{H}$₂ × 2) |
| 1.260 (40 H, m, | C$\underline{H}$₃ × 20) |
| 1.590 (4 H, m, | C$\underline{H}$₂-3' × 2) |
| 1.855 (1 H, t, J = 12.3 Hz | H-3a ax) |
| 2.058 (3 H, S, | C$\underline{H}$₃CONH—) |
| 2.300 (2 H, t, J = 7.2 Hz | C$\underline{H}$₂-2') |
| 2.315 (2 H, t, J = 7.2 Hz | C$\underline{H}$₂-2') |
| 2.744 (1 H, dd, J = 13.0, 4.6 Hz | H-3a eq) |
| 3.635 (1 H, ddd, J = 10.3, 4.8 Hz | H-4a) |
| 3.853 (3 H, S, | COOC$\underline{H}$₃) |
| 4.106 (1 H, dd, J = 12.1, 6.6 Hz | H-1) |
| 4.287 (1 H, dd, J = 12.1, 3.7 Hz | H'-1) |
| 5.145 (1 H, m, | H-2) |

(9)
3-O-[Sodium(5-acetamide-3,5-dideoxy-α-D-glycero-D-galacto-2-nonulopyranosyl)onate]-1,2-di-O-tetradecanoyl-Sn-glycerol 6.231 (1 H, d, J = 7.3 Hz)  CH₃CON$\underline{H}$)

EXAMPLE 7

Production of Compound (10) (M=Na, m, n=12)

(8)

(10)
3-O-[Sodium(5-acetamido-3,5-dideoxy-β-D-glycero-D-galacto-2-nonulopyranosyl)-onate]-1,2-di-O-tetradecanoyl-Sn-glycerol 28.0 mg (0.03 mmol) of Compound (8) was dissolved in 0.5 ml of THF and 0.5 ml of H₂O. 30 μl (0.03 mmol) of 1N-NaOH was added to the solution under cooling and the mixture was stirred for 1 hr. The reaction mixture was neutralized to pH 8 with Amberlite IRC-50 and filtered. The resin was washed with H₂O. The filtrate was combined with the wash solution and the mixture was purified by column chromatography (Yamamura Kagaku Kenkyujo ODS 60 Å 60/200 mesh, developing solvents: H₂O and MeOH). The methanolic fraction was collected and evaporated to dryness. Then, the residue was lyophilized to give 2.1 mg (0.0025 mmol) of white powdery Compound (10) (yield: 8.3%).

The physical properties of Compound (10) were as follows:

| Rf: 0.23 (CHCl₃:MeOH:AcOH = 10:2:0.3, Merck HPTLC) 500 MHz, ¹H-NMR, CDCl₃ + CD₃OD (1:1), TMS | |
|---|---|
| 0.889 (6 H, t, J = 7.0 Hz | C$\underline{H}$₃ × 2) |
| 1.300 (40 H, m, | C$\underline{H}$₂ × 20) |
| 1.650 (4 H, m, | C$\underline{H}$₂-3' × 2) |
| 2.040 (3 H, S, | C$\underline{H}$₃CONH) |
| 5.200 (1 H, m, | H-2) |

EXAMPLE 8

Production of Compound (11) (M=Na, m, n=12)

(11)

25.0 mg (0.03 mmol) of Compound (9) was dissolved in 1 ml of THF and 0.5 ml of H₂O. 30 μl (0.03 mmol) of 1N-NaOH was added to the solution under cooling and the mixture was stirred for 1 hr. The reaction mixture was neutralized to pH 8 with Amberlite IRC-50 and filtered. The resin was washed with H₂O. The filtrate was combined with the washing solution and the mixture was purified by column chromatography (Yamamura Kagaku Kenkyujo ODS 60 Å 60/200 mesh, developing solvents: H₂O and MeOH). The methanolic fraction was collected, the solvent was evaporated and the residue was lyophilized to give 5.9 mg (0.007 mmol) of white powdery Compound (11) (yield: 23.2%).

The physical properties of Compound (11) were as follows:

| Rf: 0.12 (CHCl₃:MeOH:AcOH = 10:2:0.3, Merck HPTLC) 500 MHz, ¹H-NMR, CDCl₃ + CD₃OD (1:1) TMS | |
|---|---|
| 0.889 (6 H, t, J = 7.0 Hz | C$\underline{H}$₃ × 2) |
| 1.300 (40 H, m, | C$\underline{H}$₂ × 20) |
| 1.650 (4 H, m, | C$\underline{H}$₂-3' × 2) |
| 2.033 (3 H, S, | C$\underline{H}$₃CONH) |
| 2.300 (4 H, m, | C$\underline{H}$₂-2' × 2) |
| 2.822 (1 H, m, | H-3a eq) |
| 4.170 (1 H, m, | H-2) |

What is claimed is:
1. A sialosyl glyceride having the following general formula:

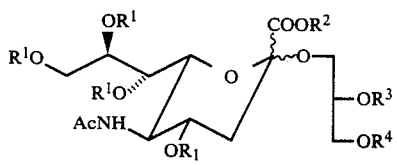

wherein R¹ represents a hydrogen atom or XCH₂CO— (X being a halogen atom), R² represents an alkali metal, a hydrogen atom or a lower alkyl group, R³ represents a hydrogen atom or —CO(CH₂)mCH₃, R⁴ represents —CO(CH₂)nCH₃ and m and n each represents a whole number of 0 to 30.

2. The sialosyl glyceride of claim 1, wherein the value m or n is 6 to 20.

3. A process for producing a sialosyl glyceride having the following general formula:

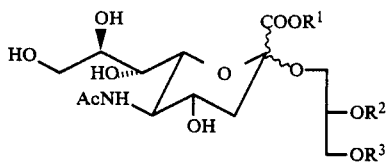

wherein R¹ represents a lower alkyl group, R² represents a hydrogen atom or —CO(CH₂)mCH₃, R³ represents —CO(CH₂)nCH₃ and m and n each represents a whole number of 0 to 30,
characterized by demonohalogenoacetylating a compound having the following general formula:

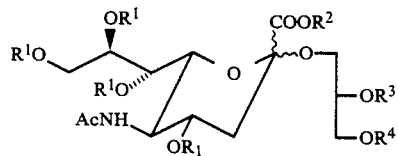

wherein R¹ represents XCH₂CO— (X being a halogen atom), R² represents a hydrogen atom or an alkyl group, R³ represents a hydrogen atom or —CO(CH₂)mCH₃, R⁴ represents —CO(CH₂)nCH₃ and m and n each represents a whole number of 0 to 30.

4. The process of claim 3, wherein the value m or n is 6 to 20.

5. A process for producing a sialosyl glyceride having the following formula:

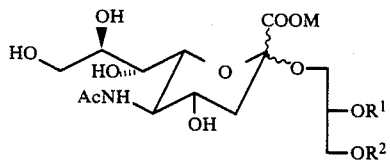

wherein M represents an alkali metal, R¹ represents a hydrogen atom or —CO(CH₂)mCH₃, R² represents —CO(CH₂)nCH₃ and m and n each represents a whole number of 0 to 30,
characterized by treating a compound having the following general formula:

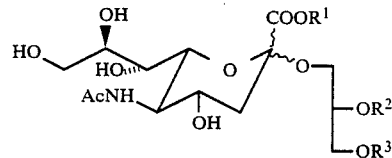

wherein R¹ represents a lower alkyl group, R² represents a hydrogen atom or —CO(CH₂)mCH₃, R³ represents —CO(CH₂)nCH₃ and m and n each represents a whole number of 0 to 30,
with an alkaline aqueous solvent.

6. The process of claim 5, wherein the value m or n is 6 to 20.

7. A sialosyl glyceride having the following general formula:

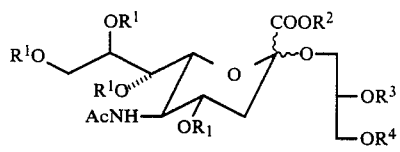

wherein R¹ represents a hydrogen atom or XCH₂CO— (X being a halogen atom), R² represents an alkali metal, a hydrogen atom or a methyl group, R³ represents a hydrogen atom or —CO(CH₂)mCH₃, R⁴ represents —CO(CH₂)nCH₃ and m and n each represents a whole number of 0 to 30.

8. A process for producing a sailosyl glyceride having the following general formula:

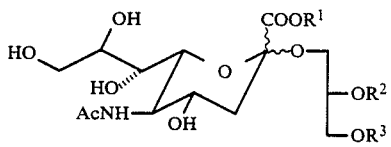

wherein R¹ represents a methyl group, R² represents a hydrogen atom or —CO(CH₂)mCH₃, R³ represents —CO(CH₂)nCH₃ and m and n each represents a whole number of 0 to 30,
characterized by demonohalogenoacetylating a compound having the following general formula:

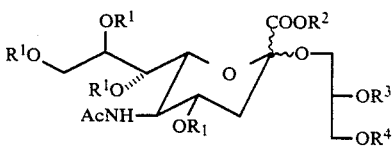

wherein R¹ represents XCH₂CO— (X being a halogen atom), R² represents a hydrogen atom or a methyl group, R³ represents a hydrogen atom or —CO(CH₂)mCH₃, R⁴ represents —CO(CH₂)nCH₃ and m and n each represents a whole number of 0 to 30.

9. A process for producing a sialosyl glyceride having the following formula:

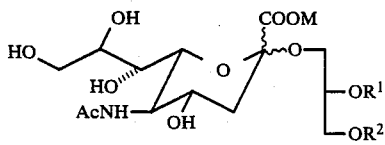

wherein M represents an alkali metal, $R^1$ represents a hydrogen atom or $-CO(CH_2)mCH_3$, $R^2$ represents $-CO(CH_2)nCH_3$ and m and n each represents a whole number of 0 to 30,
characterized by treating a compound having the following general formula:

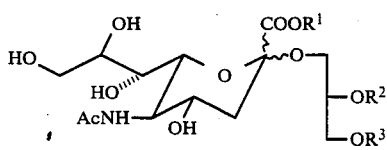

wherein $R^1$ represents a methyl group, $R^2$ represents a hydrogen atom or $-CO(CH_2)mCH_3$, $R^3$ represents $-CO(CH_2)nCH_3$ and m and n each represents a whole number of 0 to 30,
with an alkaline agueous solvent.

* * * * *